(12) United States Patent
Gunn et al.

(10) Patent No.: US 12,011,246 B2
(45) Date of Patent: *Jun. 18, 2024

(54) MULTI-CATHETER FLEXIBLE ROBOTIC SYSTEM

(71) Applicant: THE REGENTS OF THE UNIVERSITY OF CALIFORNIA, Oakland, CA (US)

(72) Inventors: Aaron Gunn, La Jolla, CA (US); Philip Weissbrod, La Jolla, CA (US); Michael Yip, La Jolla, CA (US)

(73) Assignee: THE REGENTS OF THE UNIVERSITY OF CALIFORNIA, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/075,859

(22) Filed: Dec. 6, 2022

(65) Prior Publication Data
US 2023/0098189 A1 Mar. 30, 2023

Related U.S. Application Data

(63) Continuation of application No. 16/620,007, filed as application No. PCT/US2018/036349 on Jun. 6, 2018, now Pat. No. 11,547,509.
(Continued)

(51) Int. Cl.
*A61B 34/00* (2016.01)
*A61B 18/00* (2006.01)
(Continued)

(52) U.S. Cl.
CPC .............. *A61B 34/71* (2016.02); *A61B 34/35* (2016.02); *A61M 25/0026* (2013.01);
(Continued)

(58) Field of Classification Search
CPC ... A61B 34/71; A61B 34/35; A61B 2034/301; A61M 25/0026
See application file for complete search history.

(56) References Cited

U.S. PATENT DOCUMENTS 9,364,289 B2 6/2016 Zinn
2004/0138525 A1 7/2004 Saadat
(Continued)

*Primary Examiner* — Joseph M Dietrich
*Assistant Examiner* — Michael T. Holtzclaw
(74) *Attorney, Agent, or Firm* — Stuart H. Mayer; Kaplan Breyer Schwarz LLP

(57) ABSTRACT

A multicatheter subsystem is provided for a steerable catheter robotic system. The subsystem includes a flexible output sheath, a plurality of flexible multi-lumen assemblies and a plurality of robotic instruments for performing a surgical procedure. The plurality of flexible multi-lumen assemblies extends through the outer sheath. Each of the multi-lumen assemblies has a proximal end and a distal end. Each of the robotic instruments is operatively and removably attachable to the distal end of one of the multi-lumen assemblies such that each instrument is teleoperable independently of every other robotic instrument. At least a first of the robotic instruments includes a plurality of interconnected articulating segments. Each of the articulating segments is operatively and removably attachable to a different one of the multi-lumen assemblies.

6 Claims, 6 Drawing Sheets

Related U.S. Application Data

(60) Provisional application No. 62/515,762, filed on Jun. 6, 2017.

(51) Int. Cl.
    *A61B 34/30*     (2016.01)
    *A61B 34/35*     (2016.01)
    *A61M 25/00*     (2006.01)
    *A61B 18/24*     (2006.01)

(52) U.S. Cl.
    CPC ............... *A61B 2018/00541* (2013.01); *A61B 2018/00577* (2013.01); *A61B 18/24* (2013.01); *A61B 2034/301* (2016.02); *A61B 2034/742* (2016.02); *A61B 34/76* (2016.02)

(56) References Cited

U.S. PATENT DOCUMENTS

| | | |
|---|---|---|
| 2009/0247993 A1 | 10/2009 | Kirschenman et al. |
| 2011/0238083 A1 | 9/2011 | Moll et al. |
| 2011/0288536 A1 | 11/2011 | Dejima |
| 2014/0330432 A1 | 11/2014 | Simaan et al. |
| 2015/0045812 A1 | 2/2015 | Seo |
| 2015/0250546 A1 | 9/2015 | Larkin et al. |
| 2017/0049298 A1 | 2/2017 | Hunter et al. |
| 2018/0055589 A1 | 3/2018 | Joseph et al. |
| 2018/0206711 A1* | 7/2018 | Piskun ................... A61B 1/015 |

* cited by examiner

MULTI-CATHETER FLEXIBLE ROBOTIC SYSTEM

CROSS-REFERENCE TO RELATED APPLICATIONS

This application is a continuation of U.S. Ser. No. 16/620,007, filed Dec. 6, 2019, which is a National Stage of PCT/US2018/036349, filed Jun. 6, 2018 which claims benefit of priority of U.S. Provisional Patent Application Ser. No. 62/515,762, filed Jun. 6, 2017, entitled "MULTI-CATHETER FLEXIBLE ROBOTIC SYSTEM", owned by the assignee of the present application and herein incorporated by reference in their entirety.

BACKGROUND

Remotely-controlled surgical instruments, which can include teleoperated surgical instruments (e.g., surgical instruments operated at least in part with computer assistance, such as instruments operated with robotic technology) as well as manually operated (e.g., laparoscopic, thorascopic) surgical instruments, are often used in minimally invasive medical procedures. During such procedures, a surgical instrument, which may extend through a cannula inserted into a patient's body, can be remotely manipulated to perform a procedure at a surgical site. For example, in a teleoperated surgical system, cannulas and surgical instruments can be mounted at manipulator arms of a patient side cart and be remotely manipulated via teleoperation at a surgeon console.

In the present landscape of surgical robotics, the field of continuum (or flexible) surgical robotic systems is still very much in development. These biomimetic systems, many modeled after tentacles or trunks, allow for minimally-invasive access to previously unreachable anatomy. By developing these devices with a smaller footprint and more robust laminate manufacturing techniques, lower impact surgery can be portably and efficiently performed in even tighter spaces than traditional rigid surgical robots.

SUMMARY

In accordance with one aspect of the present disclosure, a multicatheter subsystem is provided for a steerable catheter robotic system. The subsystem includes a flexible output sheath, a plurality of flexible multi-lumen assemblies and a plurality of robotic instruments for performing a surgical procedure. The plurality of flexible multi-lumen assemblies extends through the outer sheath. Each of the multi-lumen assemblies has a proximal end and a distal end. Each of the robotic instruments is operatively and removably attachable to the distal end of one of the multi-lumen assemblies such that each instrument is teleoperable independently of every other robotic instrument. At least a first of the robotic instruments includes a plurality of interconnected articulating segments. Each of the articulating segments is operatively and removably attachable to a different one of the multi-lumen assemblies.

DETAILED DESCRIPTION

As described in more detail below, a steerable catheter robotic system with a significantly reduced size-footprint is provided for deployment in field or outpatient pulmonary surgical procedures. The small size and portability of this system can help overcome a major disadvantage of current surgical robots which take up an immense amount of space in already crowded-operating rooms, while still being able to imitate, copy and improve human capabilities. In some embodiments the dimensions of the robotic instruments or tools may be as small as 1 mm.

Figure 1:
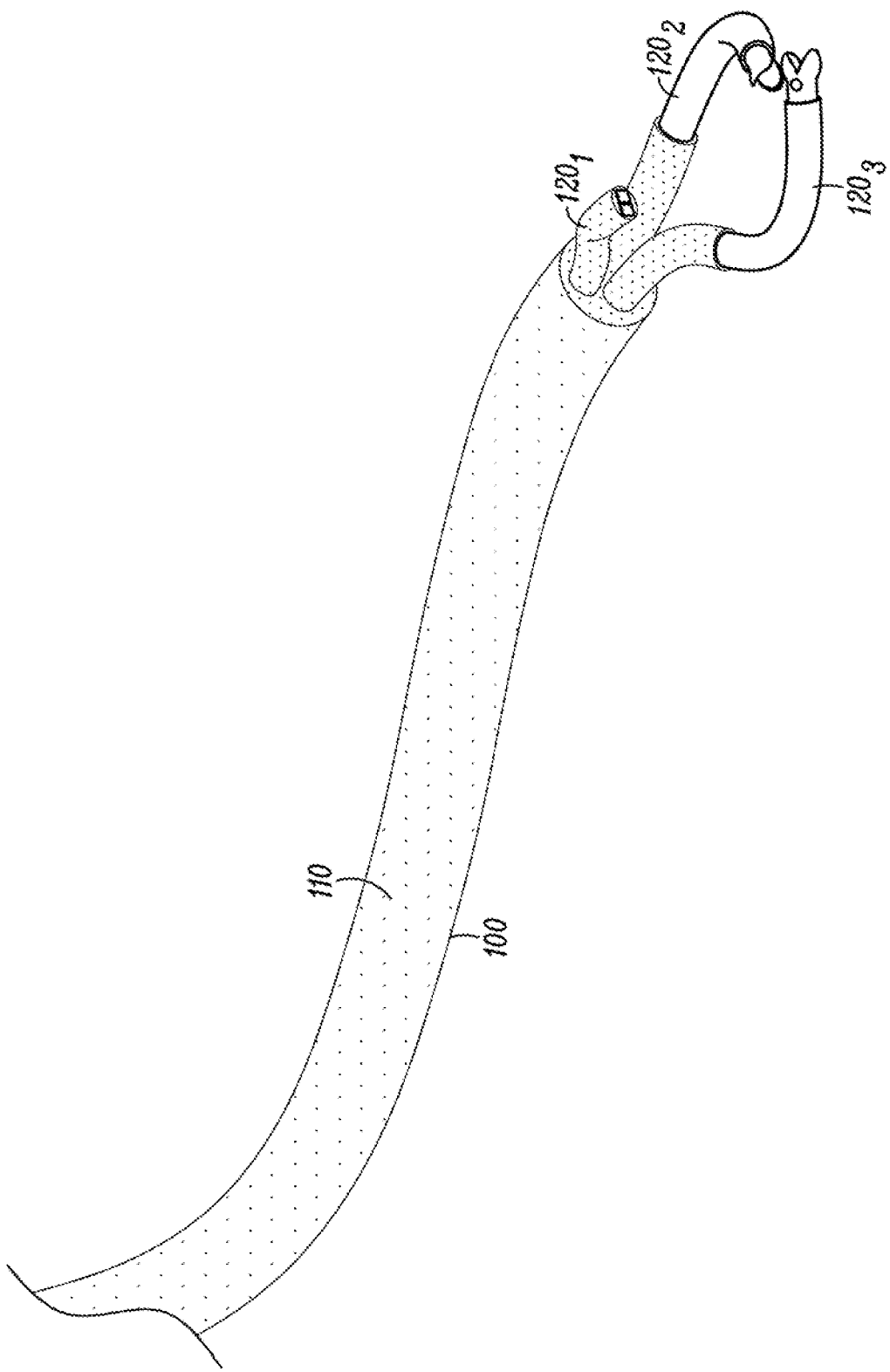
FIGS. 1 and 2 show perspective views of a multi-catheter subsystem.
Figure 2:
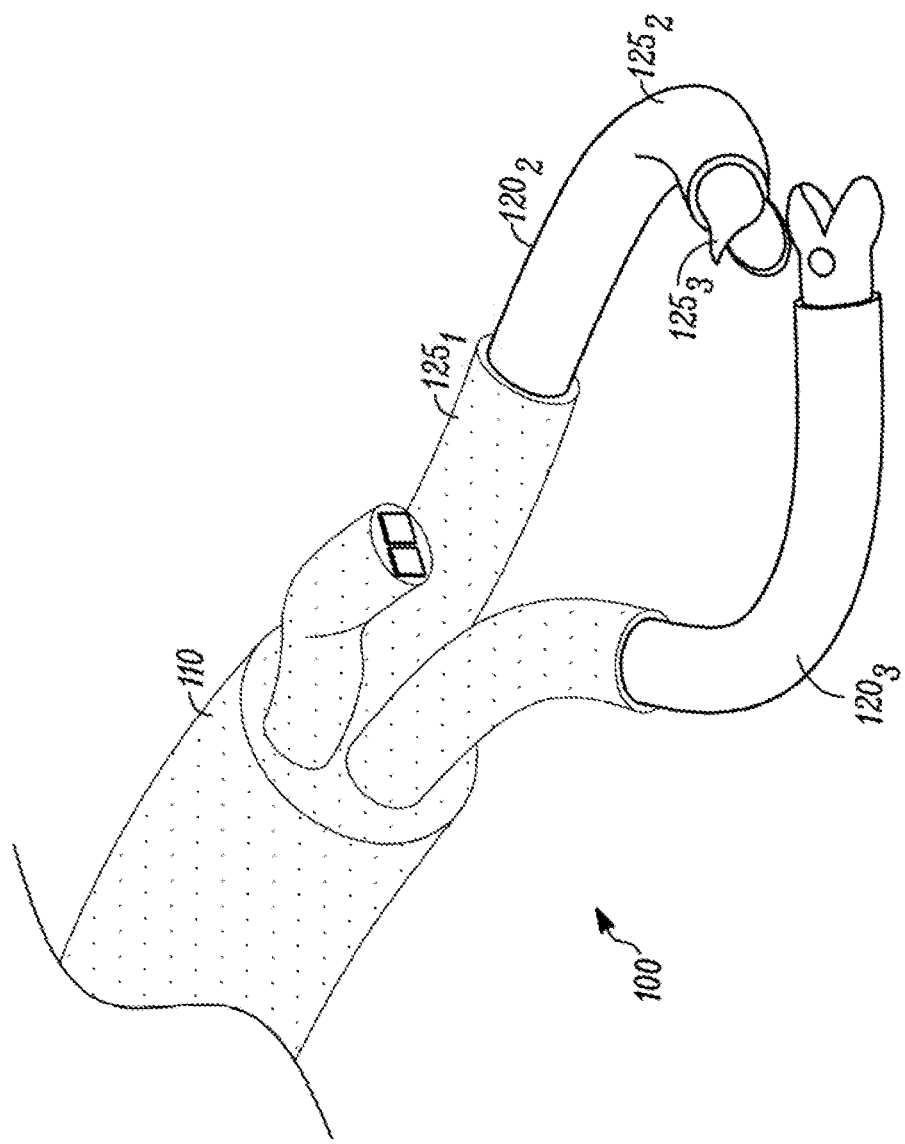

FIGS. 1 and 2 show perspective views of a multi-catheter subsystem 100 that includes a flexible outer guide shaft 110 having a distal end from which one or more robotic instruments extend. Although the embodiment shown in FIGS. 1 and 2 shows three robotic instruments $120_1$, $120_2$ and $120_3$ ("120"), more generally any number of such robotic instruments 120 may be employed. In this particular embodiment the robotic instruments 120 include a camera $120_1$ and first and second grasping forceps $120_2$ and $120_3$. A control assembly (not shown in FIGS. 1 and 2) is located at the proximal end of the outer sheath 110 controls the operation of the robotic instruments 120.

In some embodiments each robotic instrument 120 may include two or more articulating segments that provide the instrument with multiple degrees of freedom. For instance, as best seen in FIG. 2, the first grasping forcep $120_2$ includes three articulating segments $125_1$, $125_2$ and $125_3$. The second grasping forcep $120_3$ may be similarly configured. By employing a suitable number of articulating segments, some instruments may be supplied with 7 degrees of freedom of articulation (i.e. positional control of x, y, z in cartesian space, and roll-pitch-yaw in orientation, and an actuation degree of freedom such as a pinch grip of a forcep), thereby essentially recovering the dexterity of a human hand. In such an embodiment a one-to-one mappings can be advantageously realized of a teleoperating using to the robotic instrument. If more than 7 degrees of freedom are provided to a given instrument, the instrument can have additional degrees of freedom to conform to the environment without affecting the controllability of the 7 degrees of freedom that are controlled by the human operator. Some instruments may have additional elbow deflection locations that allow the shape of the instrument to better conform to the environment.

When one of the robotic instruments is a camera, it may be operated with only 6 degrees of freedom for full visual control, although the focal depth (if so integrated) may be considered a $7^{th}$ degree of freedom.

Figure 3:
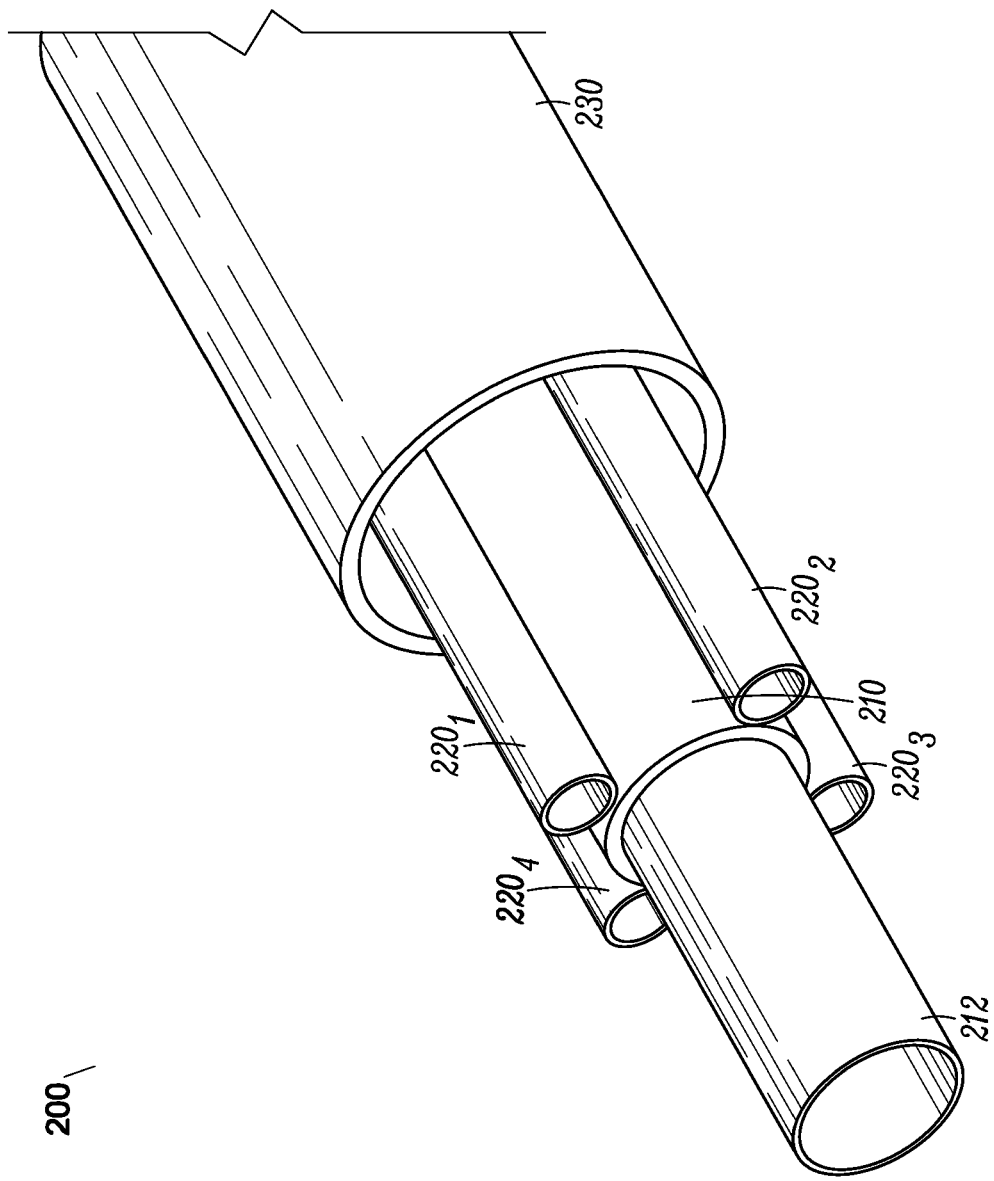
FIG. 3 shows one example of a multi-lumen assembly that is used to steer a single one of the robotic instruments shown in FIGS. 1 and 2.

FIG. 3 shows one example of a multi-lumen assembly 200 that is used to steer a single instrument 120. Each of the lumens is formed from a flexible material such as a flexible polymer. The multi-lumen assembly 200 extends through the outer guide shaft 110 shown in FIG. 1. The multi-lumen assembly 200 includes a center channel 210 that has a liner 212 that serves as an instrument port for one segment of a multi-segment instrument (or a complete instrument of a single-segment instrument). Surrounding the center channel 210 are a series of control lumens 220 through which articulation wires (not shown) extend. In this example 4 control lumens $220_1$, $220_2$, $220_3$ and $220_4$ are shown. The control lumens 220 are secured (e.g., fused) to the center channel 210. Articulation of the instrument segment located in the center channel 210 is determined by the coordinated operation of the articulation wires via the control assembly, which will be described below. The center channel 210 and the control lumens 220 may extend through a flexible sheath 230 (which itself extends through the outer guide shaft 110 shown in FIGS. 1 and 2).

Each articulating segment of a multi-segment instrument includes its own dedicated multi-lumen assembly 200 for controlling that segment. The different multi-lumen assemblies 200 of a single multi-segment instrument may be concentrically arranged with one another.

As mentioned above, the multi-lumen assembly 200 may be fabricated from flexible polymers. For example, in some embodiments the flexible sheath 230 and center channel 210 may be formed from a varying durometer thermoplastic polymer such as a polyester block amide (available, for instance, under the tradename PEBAX®). An optional stainless steel or fiber braid (not shown) may surround the flexible sheath 230. Likewise, in some embodiments the control lumens may be formed polymide and the liner 212 lining the center channel 210 may be formed from PTFE (i.e., Teflon®). The use of flexible polymers for the multi-lumen assembly affords significant flexibility in short segments without deterioration of the assembly and tight radiuses of curvatures can be achieved. Lamination of these polymers, which can become micron-thickness layers, enables these robotically controlled lumens to reach as small as 1 mm in diameter.

Figure 4:
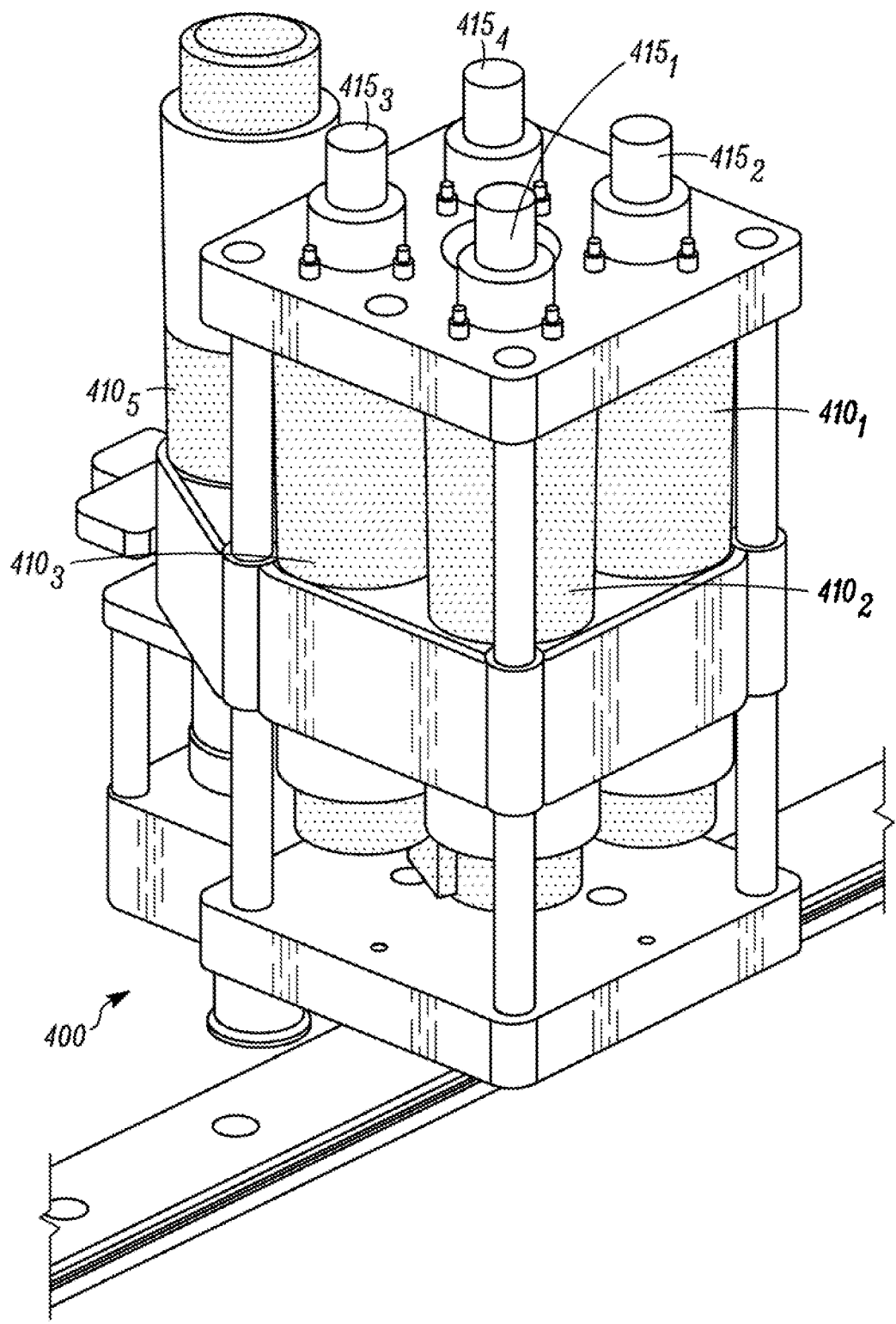
FIG. 4 shows a motor control assembly.
Figure 5:
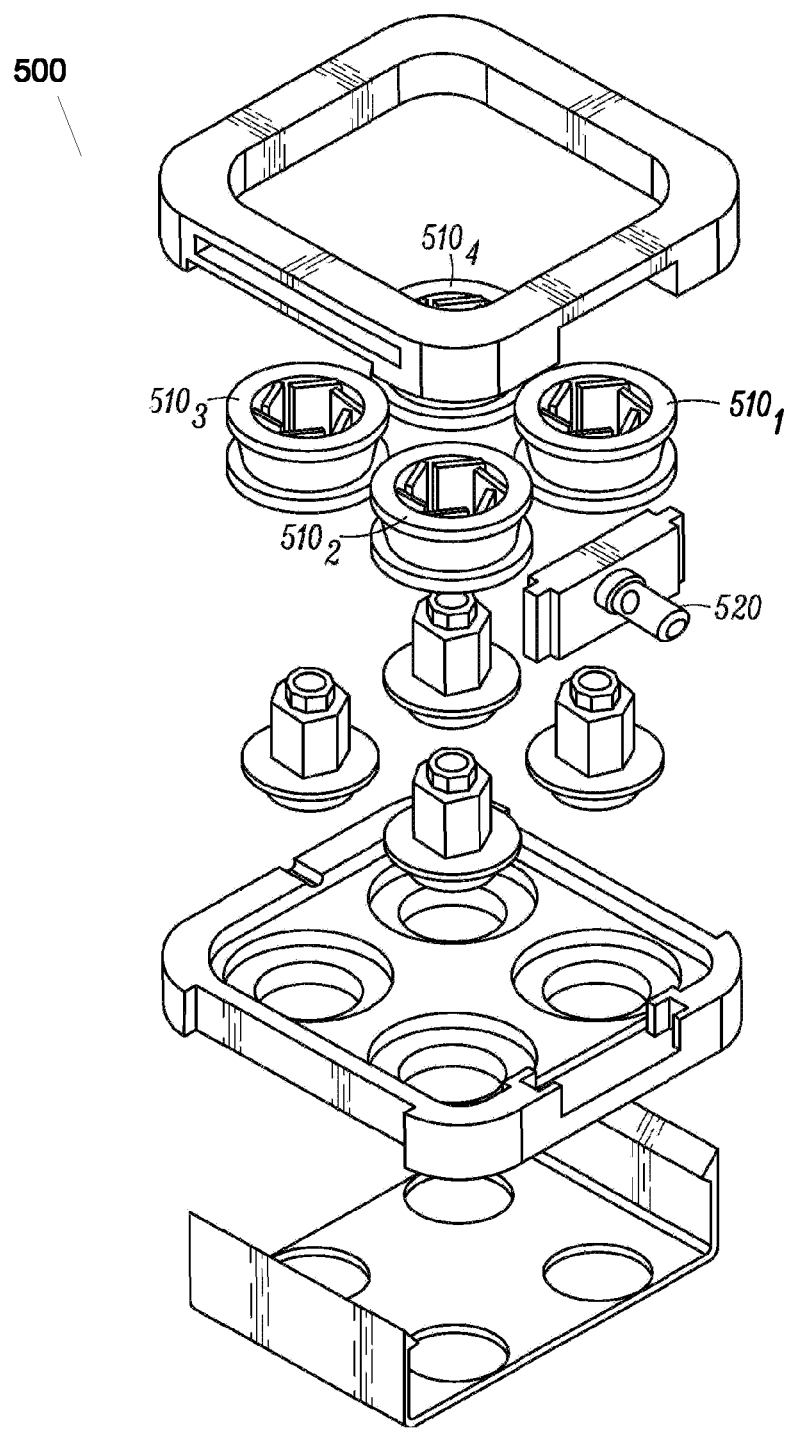
FIG. 5 shows a pully housing assembly.

FIG. 4 shows a motor control assembly 400 that can be used in conjunction with a pully housing assembly 500 (FIG. 5) to control the four pull wires that extend through the control lumens 220. The motor control assembly 400 includes four motors $410_1$, $410_2$, $410_3$ and $410_4$ (where motor $410_4$ is not visible in FIG. 4). that each respectively control the rotation of a rotatable shaft $415_1$, $415_2$, $415_3$ and $415_4$. The pully housing assembly 500 includes four torque-limiting pulleys $510_1$, $510_2$, $510_3$ and $510_4$. When the pulley housing assembly 500 is mated with the motor control assembly 400 each pulley $510_1$, $510_2$, $510_3$ and $510_4$ is axially mounted on one of the shafts $415_1$, $415_2$, $415_3$ and $415_4$. The pulley housing assembly 500 also includes a shaft mount 520 onto which is mounted the outer guide shaft 110 and the multi-lumen assemblies 200 extending therethrough. Once installed, rotational actuation of the motors 410 located in the motor control assembly 420 is translated to linear actuation, providing four degrees of freedom to each instrument segment.

The motor control assembly 400 includes an additional motor 4105 that is used to extend and retract the robotic instrument under its control.

The control of the robotic instruments is accomplished using inverse kinematics to map Cartesian coordinates into the positions of the four pull wires. Coordinates are first multiplied by a dynamically adjustable rotation matrix, and then by constants derived during a simple calibration process in order to standardize actuation across multiple instruments. A position-based control approach using analog values to scale targets in Cartesian space that are then mapped to $R^4$, resulting in high position accuracy along with precise control over actuation velocity. The final result is accurate and intuitive control over two degrees of freedom per instrument, all mapped to a user interface.

Figure 6:
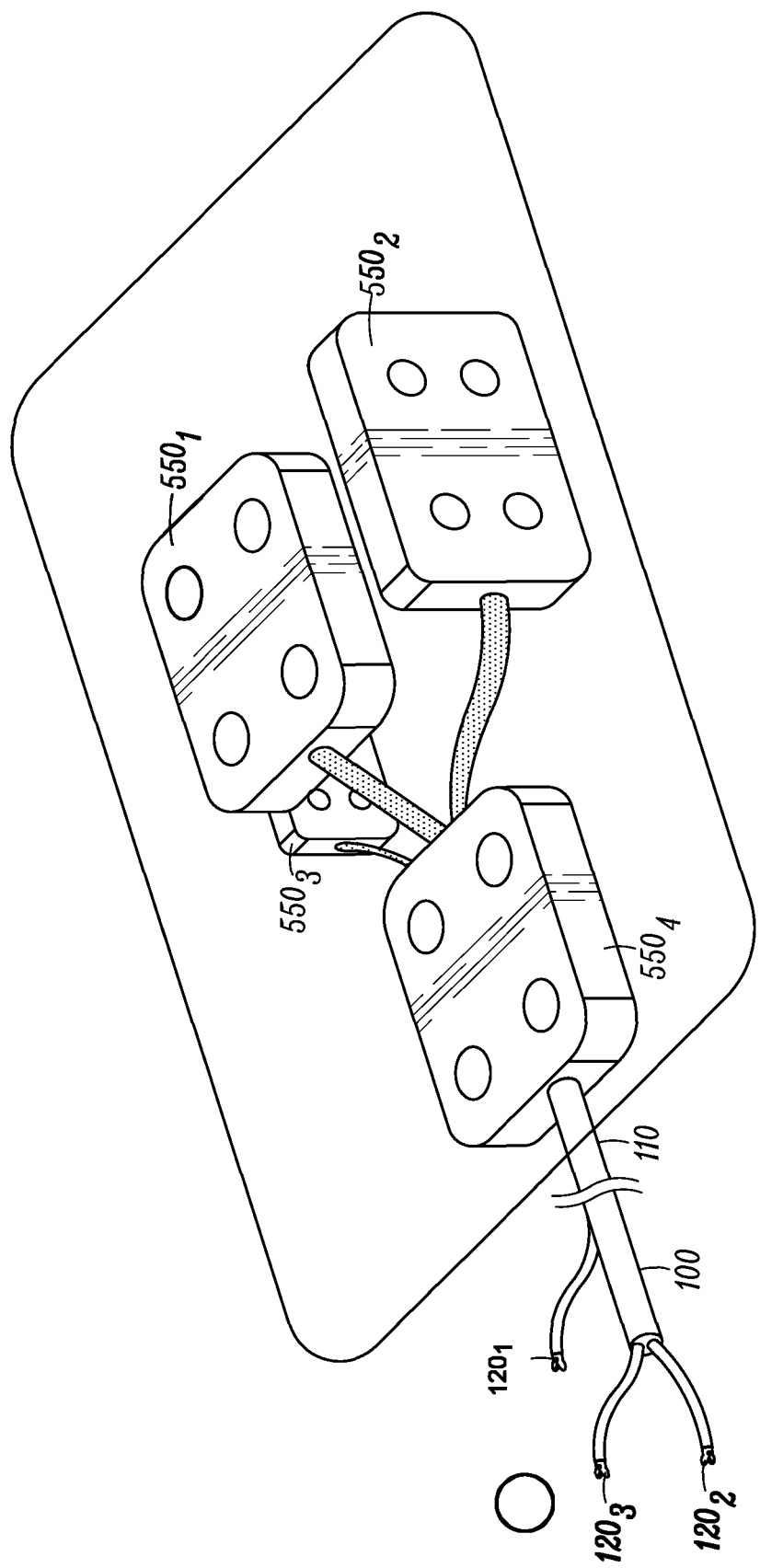
FIG. 6 shows an example of a steerable catheter robotic system that includes the multi-catheter subsystem shown in FIGS. 1 and 2.

FIG. 6 shows an example of the steerable catheter robotic system that includes the multi-catheter subsystem 100 shown in FIGS. 1 and 2, which includes the three instruments $120_1$, $120_2$ and $120_3$. Like reference numerals shown in FIG. 6 and the remaining figures denote like elements. As shown, the proximal end of the multi-catheter subsystem 100 includes controllers $550_1$, $550_2$, $550_3$ and $550_4$ ("550"). Each controller 550 includes one of the motor control assemblies 400 mated with one of
- the pulley housing assemblies 500. Controller $550_1$ is used to
- control instrument $120_1$, controller $550_2$ is used to
- control instrument $120_2$ and controller $550_3$ is used to control instrument $120_3$. The additional controller $550_4$ is used to control the overall movement of the multi-catheter subsystem 100.

Control of the steerable catheter robotic system via a user interface (not shown) focuses on two distinct tasks: robot movement and multiple catheter articulation. Both movements can be controlled from a single console. For instance, in one embodiment the operator is able to advance the robot via a haptic joystick. The path of the multi-catheter subsystem can be visualized on a display of the user interface console. The display may include a high-definition or 3-D screen. Additional screens within the console may allow for projection of imaging studies or electromagnetic instrument registration for use during the procedure being performed. The joystick allows forward and backward movement and 180° movement in an x and y plane of the distal tip. To prevent traumatic navigation, haptic feedback may be provided which is associated with the platform movement. Once positioned in the desired location, the platform can be fixed to allow stability during instrument insertion and movement.

As discussed above, in one embodiment there are two articulating instruments that can be inserted through the length of the multi-catheter subsystem. Movement of each instrument is controlled by independent finger grasping interfaces. The instruments can be advanced or withdrawn by depression or retraction of a grasping unit. In instances where there are no grasping movements, the instruments may be moved as if grasping a virtual pencil.

A wide variety of different interchangeable robotic instruments may be used in the multi-catheter subsystem. Examples of such instruments include, without limitation, biopsy cups, grasping forceps, injection needles, biopsy needles, laser introducers, basket retrievers, hot knives, clip appliers, and scissors. The instrument or instruments that are used will be application-dependent. Examples of such applications include laryngeal, pharyngeal, hypopharyngeal, tracheal, bronchial, esophageal, stomach, large and small bowel applications. Additionally, applications include newer advanced endoscopic procedures, including endoluminal tumor ablation in varying anatomic locations, Peroral Endoscopic Myotomy (POEM), and Natural Orifice Transluminal Endoscopic Surgery (NOTES).

Robotic instruments may be interchangeable so that the multi-catheter subsystem 100 can swap the types and locations of instruments as required to generate different configurations for a user to extend their ability to work with tissues in a narrow space, extend their reach, improve their visual range, or improve the ergonomics of control. The software controlling the multi-catheter sub-system may reposition its coordinate frame to match an intuitive viewpoint of the teleoperator.

In some cases it is possible that the system can introduce more robotic instruments than a single user can control. In this scenario, both a primary user and an assistant may operate different instruments through the same system, enabling multiple robotic instruments to be controlled simultaneously. This encourages shared tasks, allowing assistants to help with the retraction of objects or environmental roadblocks while the primary user is operating on the exposed area.

One embodiment of the system may involve the autonomous control of one instrument that follows or performs some assistive task that follows the behavior of a primary user. For example, a continuous ablation using a laser that reaches deeper within a site may be realized by having one of the robotic instruments follow a user-controlled ablation probe as it moves through the environment, i.e., a robotically controlled camera. In this case one instrument would be teleoperated while the other is autonomous and following the teleoperated camera.

The ability to simultaneously control and steer multiple robotic instruments can provide critical capabilities in manipulating areas of tissues with bimanual manipulation. For example, controlled stretching of tissue or peeling of tissue can be achieved only with two or more instruments. Likewise, the ability to mount and control a camera independently of the other instruments (and vice-versa) is a significant advantage over current endoscopic approaches where the endoscope is the camera and dictates the controllability of the instruments exiting from its orientation-fixed instrument lumen. Moreover, the multi-catheter system may be mixed with manual instrumentation given that the instrumentation fits within the available lumens for control.

Another advantage of the steerable catheter robotic system described herein is that one of its intracorporeal instruments can be used to stabilize another when there is a desire for improved stiffness. For example, an outstretched robotic instrument may become too compliant to lift a tissue that is far away. A support provided from a second robotic instrument may be devised to generate mechanical leverage that can amplify the force generation or the reachability of the original, unsupported instrument. In the same way, the robotic instruments may be used to support the sub-system in general and create anchors to provide stabilization against patient or anatomical motions or more generally to combat moment-arm effects.

Yet another advantage of the steerable catheter robotic system described herein arises in those embodiments that are fabricated exclusively from polymer or other non-metallic materials since these embodiments may be used in conjunction with magnetic resonance imaging (MRI) techniques.

Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. If the specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

The invention claimed is:

1. A multicatheter subsystem for a steerable catheter robotic system, comprising:
    a flexible outer sheath having a proximal end and a distal end;
    a plurality of flexible multi-lumen assemblies extending through the flexible outer sheath, each of the multi-lumen assemblies having a proximal end and a distal end;
    a plurality of robotic instruments for performing a surgical procedure, each of the robotic instruments being operatively and removably attachable to the distal end of one of the multi-lumen assemblies such that each of the robotic instruments is teleoperable independently of every other robotic instrument, at least a first of the robotic instruments including a plurality of interconnected articulating segments, each of the articulating segments being operatively and removably attachable to a different one of the multi-lumen assemblies.

2. The multicatheter subsystem of claim 1 wherein the first instrument is configured to have 7 degrees of freedom.

3. The multicatheter subsystem of claim 1 wherein the flexible outer sheath, the plurality of flexible multi-lumen assemblies and the plurality of robotic instruments are formed from polymer materials.

4. The multicatheter subsystem of claim 1 wherein each of the multi-lumen assemblies includes at least one actuating arrangement for steering the instrument attached thereto.

5. The multicatheter subsystem of claim 4 further comprising a control assembly operatively coupled to the proximal end of the multi-lumen assemblies for providing rotational movement that imparts translational movement to the actuating arrangement.

6. The multicatheter subsystem of claim 5 wherein at least one of the actuating arrangements includes:
    a plurality of control lumens attached to and surrounding a central lumen to which one of the instruments is removably attached; and
    a plurality of pull wires each extending through one of the control lumens, a proximal end of each of the pull wires being operatively connected to the control assembly.

\* \* \* \* \*